US010758212B2

(12) United States Patent
Wiemker et al.

(10) Patent No.: US 10,758,212 B2
(45) Date of Patent: Sep. 1, 2020

(54) AUTOMATIC DEPTH SCROLLING AND ORIENTATION ADJUSTMENT FOR SEMI-AUTOMATED PATH PLANNING

(71) Applicant: KONINKLIJKE PHILIPS N.V., Eindhoven (NL)

(72) Inventors: Rafael Wiemker, Kisdorf (DE); Kongkuo Lu, Briarcliff Manor, NY (US); Sheng Xu, Rockville, MD (US); Tobias Klinder, Uelzen (DE); Martin Bergtholdt, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 896 days.

(21) Appl. No.: 14/361,884

(22) PCT Filed: Nov. 28, 2012

(86) PCT No.: PCT/IB2012/056781
§ 371 (c)(1),
(2) Date: May 30, 2014

(87) PCT Pub. No.: WO2013/080131
PCT Pub. Date: Jun. 6, 2013

(65) Prior Publication Data
US 2014/0344742 A1 Nov. 20, 2014

Related U.S. Application Data

(60) Provisional application No. 61/566,609, filed on Dec. 3, 2011.

(51) Int. Cl.
A61B 10/02 (2006.01)
G06F 3/0481 (2013.01)
(Continued)

(52) U.S. Cl.
CPC .......... *A61B 10/0233* (2013.01); *A61B 34/10* (2016.02); *A61B 34/25* (2016.02);
(Continued)

(58) Field of Classification Search
CPC ........ A61B 2034/101; A61B 2034/107; A61B 2090/365; A61B 34/10; A61B 34/25;
(Continued)

(56) References Cited

U.S. PATENT DOCUMENTS 5,371,778 A * 12/1994 Yanof ................. G06F 3/04845
128/922
5,611,025 A 3/1997 Lorensen et al.
(Continued)

FOREIGN PATENT DOCUMENTS

CN 101170961 A 4/2008
JP 10057370 A 2/1998
(Continued)

OTHER PUBLICATIONS

T. Bulow, et al., "A General Framework for Tree Segmentation and Reconstruction from Medical Volume Data", Philips Research Laboratories, Roetgenstrasse 24-26, D-22335, Hamburg, Germany, undated.
(Continued)

*Primary Examiner* — Arpan P. Savla
*Assistant Examiner* — Parmanand D Patel
(74) *Attorney, Agent, or Firm* — Sherry Austin

(57) ABSTRACT

A planning tool, system and method include a processor (114) and memory (116) coupled to the processor which stores a planning module (144). A user interface (120) is coupled to the processor and configured to permit a user to select a path through a pathway system (148). The planning module is configured to upload one or more slices of an image volume (111) corresponding to a user-controlled cursor point (108) guided using the user interface such that
(Continued)

as the path is navigated the one or more slices are updated in accordance with a depth of the cursor point in the path.

29 Claims, 7 Drawing Sheets

(51) Int. Cl.
 G06F 3/0484 (2013.01)
 G06T 19/00 (2011.01)
 A61B 34/10 (2016.01)
 A61B 34/00 (2016.01)
 G16H 40/40 (2018.01)
 A61B 90/00 (2016.01)

(52) U.S. Cl.
 CPC ........ *G06F 3/0481* (2013.01); *G06F 3/04842* (2013.01); *G06T 19/003* (2013.01); *G16H 40/40* (2018.01); *A61B 2034/101* (2016.02); *A61B 2034/107* (2016.02); *A61B 2090/365* (2016.02); *G06T 2210/41* (2013.01)

(58) Field of Classification Search
 CPC ... A61B 19/50; A61B 10/0233; G06F 3/0481; G06F 19/3412; G06T 19/00
 See application file for complete search history.

(56) References Cited

U.S. PATENT DOCUMENTS

| | | | |
|---|---|---|---|
| 5,891,030 A | | 4/1999 | Johnson et al. |
| 6,505,065 B1 | | 1/2003 | Yanof et al. |
| 8,166,971 B2 | | 5/2012 | Jaffe et al. |
| 9,036,882 B2* | | 5/2015 | Masumoto ........... A61B 5/4255 382/128 |
| 2002/0118869 A1 | | 8/2002 | Knoplioch et al. |
| 2005/0033117 A1 | | 2/2005 | Ozaki et al. |
| 2005/0245803 A1* | | 11/2005 | Glenn, Jr. ........... A61B 5/4255 600/407 |
| 2006/0084860 A1* | | 4/2006 | Geiger ................. A61B 10/04 600/407 |
| 2007/0049861 A1 | | 3/2007 | Gundel |
| 2007/0060792 A1 | | 3/2007 | Draxinger et al. |
| 2007/0276214 A1* | | 11/2007 | Dachille .............. G06T 7/0012 600/407 |
| 2008/0118135 A1 | | 5/2008 | Averbuch et al. |
| 2008/0183073 A1 | | 7/2008 | Higgins et al. |
| 2008/0302364 A1 | | 12/2008 | Garde et al. |
| 2009/0209809 A1 | | 8/2009 | Schaller et al. |
| 2010/0008555 A1* | | 1/2010 | Trumer ................. A61B 34/25 382/131 |
| 2010/0085555 A1 | | 4/2010 | Schmid et al. |
| 2010/0160733 A1 | | 6/2010 | Gilboa |
| 2011/0029248 A1 | | 2/2011 | Saeed et al. |
| 2011/0040175 A1* | | 2/2011 | Shahidi ................. A61B 5/064 600/424 |
| 2013/0204099 A1 | | 8/2013 | Colman et al. |
| 2014/0330155 A1 | | 11/2014 | Brewer et al. |
| 2015/0165145 A1 | | 6/2015 | Alder et al. |

FOREIGN PATENT DOCUMENTS

| | | |
|---|---|---|
| JP | 2003265408 A | 9/2003 |
| JP | 2005110973 A | 4/2005 |
| JP | 2008054763 A | 3/2008 |
| JP | 2010510815 A | 4/2010 |
| WO | WO2005008591 | 1/2005 |
| WO | 2008068107 A1 | 6/2008 |
| WO | WO2008095068 | 8/2008 |
| WO | WO2009138871 | 11/2009 |
| WO | WO2010140074 | 12/2010 |

OTHER PUBLICATIONS

"SuperDimensions iLogic Promotional Video", Jun. 8, 2010, via Youtube.com, www.youtube.com/watch? v=3oCkvD8eaMQ.

"SuperDimension Planning Phase", Jan. 14, 2009, via Youtube.com, www.youtube.com/?v=r_Zdpfh-Xww.

R. Wiemker, et al., "A Simple Centricity-Based Region Growing Algorithm for the Extraction of Airways", EXACT ;09, Philips Research Lab Hamburg, Rontgenstrasse 24, 22355 Hamburg, Germany, pp. 309-314, undated.

* cited by examiner ial Application Serial
AUTOMATIC DEPTH SCROLLING AND ORIENTATION ADJUSTMENT FOR SEMI-AUTOMATED PATH PLANNING

CROSS-REFERENCE TO PRIOR APPLICATIONS

This application is the U.S. National Phase application under 35 U.S.C. § 371 of International Application Serial No. PCT/IB2012/056781, filed on Nov. 28, 2012, which claims the benefit of U.S. Application Ser. No. 61/566,609, filed on Dec. 3, 2011. These applications are hereby incorporated by reference herein.

This disclosure relates to medical instruments and more particularly to systems and methods for graphically planning and assisting medical procedures using a graphical interface tool.

Transbronchial biopsies are a common interventional procedure where a biopsy needle is delivered in a working channel of a bronchoscope and is advanced through an airway wall at some point to retrieve a specimen of a tumor, lymph node, etc. in the lung or mediastinum. To assist the planning as well as the real-time guidance of such an intervention, a thoracic scan of the patient is performed. The scan, such as a computed tomography (CT) scan, can be displayed to a user (e.g., a pulmonologist) in radiological Standard Views as well as in virtual renderings of an Endoluminal-View, similar to the optical images of a real bronchoscope camera.

In the Endoluminal-View, for an optical image from a real endoscopy or a virtual rendering, the user cannot see tissue behind the airway wall, in particular, the location of the biopsy target or the locations of vessels which are not to be punctured. Similarly, in the Standard View, the user cannot see exactly where a certain point would be located in the Endoluminal View.

Semi-automated path planning for bronchoscopies requires the manual setting of a number of path points in a three-dimensional CT image volume. For the setting of these path points in a two-dimensional display, the user needs to control three position and three orientation parameters of the currently displayed view plane. This considerably slows the workflow.

Path planning for bronchoscopies to peripheral targets (e.g., for biopsies) is a common but difficult clinical task. Fully automated path planning between a target and a trachea is desirable but may not always deliver optimal results. In contrast, semi-automated manual path planning requires the setting of a number of path points in three-dimensional CT image volumes.

In accordance with the present principles, a planning tool, system and method include a processor and memory coupled to the processor which stores a planning module. A user interface is coupled to the processor and configured to permit a user to select a path through a pathway system. The planning module is configured to upload one or more slices of an image volume corresponding to a user-controlled cursor point guided using the user interface such that as the path is navigated the one or more slices are updated in accordance with a depth of the cursor point in the path.

A system having operatively coupled viewports includes a processor and memory coupled to the processor, which stores an image processing module. A graphical user interface is coupled to the processor and configured to permit a user to select a path through a pathway system. The image processing module is configured to render an endoluminal view of the pathway, one or more other views of an image volume and a virtual line to provide a spatial reference in all selected views including the endoluminal view and the one or more other views. A user-controlled cursor point is configured to guide the endoluminal view wherein the cursor point is employed to permit updates in all the selected views corresponding to a selection update in the cursor point such that image information surrounding the cursor point in other views is concurrently viewable in the user interface.

A method for planning a procedure includes locating an end point in an image volume of a pathway structure, the image volume comprised of stacked slices along a depth; selecting a start point in the image volume of the pathway structure; extending a path along the pathway structure; updating image slices of the pathway structure along the path in accordance with a depth of the pathway structure corresponding with the image slices; navigating along the pathway to the end point; and storing the path for creating a plan for a procedure.

A method for operatively coupling viewports includes generating an endoluminal view of a pathway structure in a graphical user interface configured to permit a user to select a path through a pathway system; generating one or more other views of an image volume; and generating a virtual line to provide a spatial reference in a plurality of views including the endoluminal view and the one or more other views such that the virtual line is configured to guide the endoluminal view and is employed to provide a reference to permit updates in the other views corresponding to a user selected position update of the virtual line such that image information surrounding the virtual line in the other views is concurrently viewable in the user interface.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
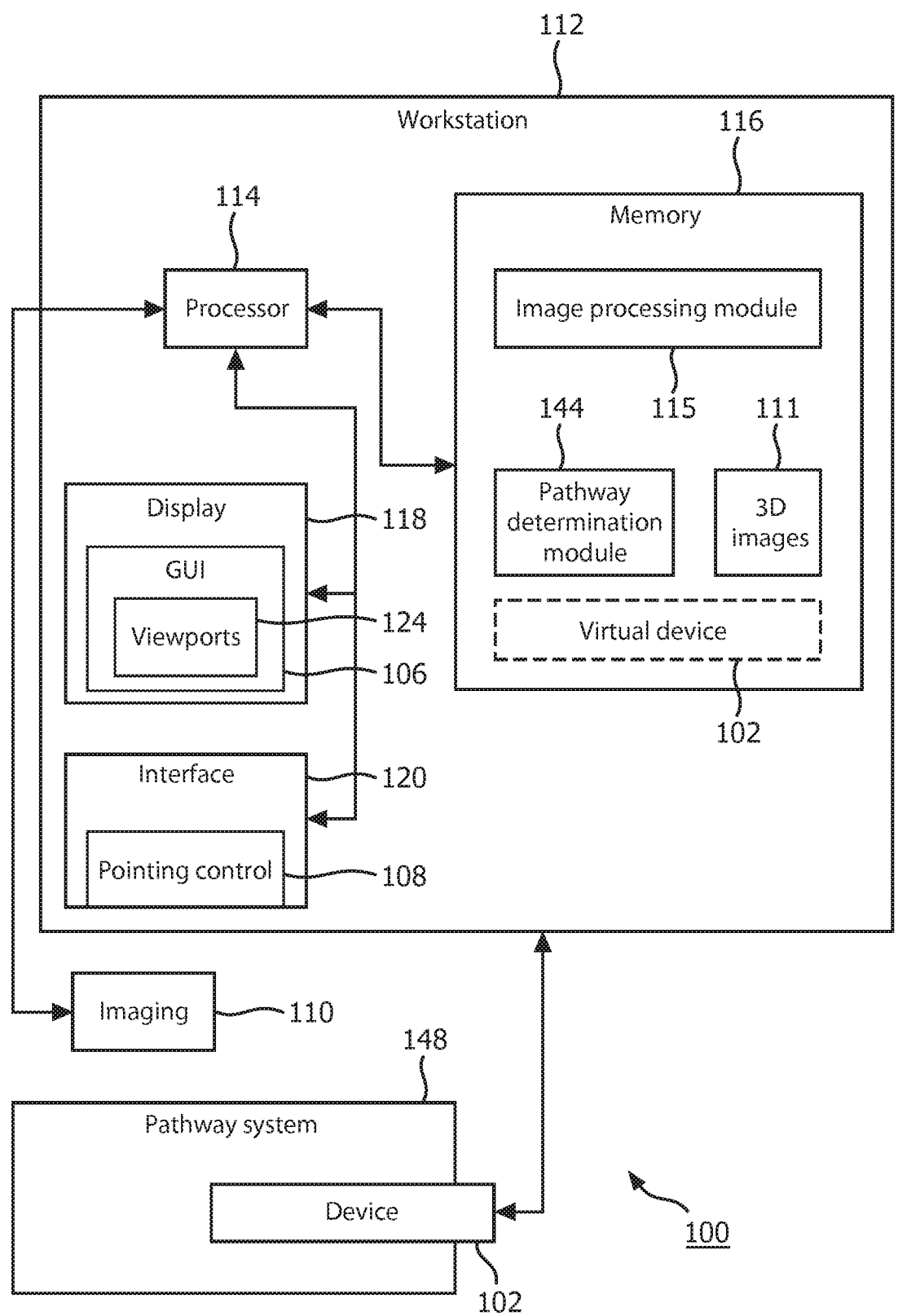
FIG. 1 is a block/flow diagram showing a system/method for planning a procedure and concurrently viewing linked display views of different perspectives in accordance with one embodiment.

In accordance with the present principles, a system with a graphical user interface is provided having an automatic adaptation of depth, position and orientation of a currently displayed view plane, so that a user only needs to control a two-dimensional tracking of an internal structure, such as in an airway of a lung. The view plane can be updated continuously. A method performs a local tracing of the structure using a mouse or similar pointing device, using the mouse movement to automatically change a position of the displayed view plane and its orientation. A mouse point is located centrally in the structure (e.g., airway) and a view plane orientation is aligned with the structure's orientation. In this way, the user can mouse-drag a path from a target (e.g., a biopsy target) to a start position (e.g., a trachea) without needing to adjust the view plane control parameters. This graphical user interface and underlying methods create a much more efficient and easier to interpret workflow.

A three-dimensional input image volume, e.g., a CT scan, is normally displayed only in the form of one or more planar slice images. The only possibilities includes x, y and z axis-aligned images (axial, coronal, sagittal), oblique planar or curved reformat images. Within these two-dimensional view planes, the user can click into pathway locations to set or edit path control points. For a manual setting of these path points in a two-dimensional display, the user needs to control three position parameters and three orientation parameters of a currently displayed view plane. In particular, the user needs to scroll through slices (to adjust a depth position of the currently displayed slice) and to change the orientation (e.g., rotation around the cranio-caudal body axis), to achieve optimal visibility and traceability of the pathway. Substantial user interaction is needed, and this considerably delays the workflow for setting the control points.

In one embodiment in accordance with the present principals, a graphical user interface (GUI) includes a continuous automatic adaptation of the depth position and orientation of the currently displayed view plane. When a user drags a pointer or mouse inside a pathway, a depth position of the currently displayed view plane is automatically adjusted such that the mouse point remains central in the local pathway. Optionally, the displayed view plane is also rotated around the current mouse point such that a local direction of the airway is optimally aligned with the displayed slice view plane.

This workflow includes that the user places the mouse point at a target, and then drags the mouse along the pathway up to a start point (e.g., a trachea) without having to adjust any other view control parameters at all. The user controls only the two-dimensional tracking of the pathway in the view plane, with depth and rotation adapted automatically. This is achieved by an underlying algorithm or method, which for each new mouse position performs a local tracing of the pathway in which the mouse point is currently located. A 3D-centerpoint of the local pathway and its local orientation are determined. If there is a difference between currently displayed depth or orientation and the estimated pathway center and orientation, then the view plane parameters are changed accordingly, and the display is updated in real-time (e.g., live feedback).

In another embodiment, a graphical user interface (GUI) includes several viewports or panes which permit movement in a virtual Endoluminal-View similar to image feedback from a real endoscopy. The viewports offer oblique reformats to show, for each point in the Endoluminal-View, which tissue would be traversed if a virtual needle would be advanced through a pathway wall point being displayed in the image pane. This serves to find an appropriate biopsy path leading to a target (e.g., a targeted tumor or lymph node) while avoiding critical tissues and vessels.

In this embodiment, virtual and real Endoluminal-Views are interactively coupled to and between viewports. The tissue which would be penetrated by a needle advanced from a current point of view (camera point) is correlated to real or virtual images in other views. A virtual needle or other reference is specified by a current mouse position in the Endoluminal-View, and an automatic computation and display of appropriate needle-oriented oblique Reformat-Views is provided. The capability to advance the camera position in the Endoluminal-View without penetrating the airway wall, using the depth information underlying the Endoluminal-View is also achieved.

It should be understood that the present invention will be described in terms of medical instruments; however, the teachings of the present invention are much broader and are applicable to any systems and methods where pathway navigation is performed. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Referring now to the drawings in which like numerals represent the same or similar elements and initially to FIG. 1, a system 100 for graphical path planning and device tracking is illustratively shown in accordance with one embodiment. The system 100 may be employed in image display modules in medical workstations, and is particularly useful with dedicated bronchoscopy software suites (e.g., interventional cockpits) or for blood vessel tracing (e.g., embolism and plaque inspection). Other applications are also contemplated.

System 100 may include a workstation or console 112 from which a procedure is supervised and/or managed. Workstation 112 preferably includes one or more processors 114 and memory 116 for storing programs and applications. Memory 116 may store an image processing module 115 configured to generate virtual instruments, to conform multiple viewports for viewing images from a real camera, image volumes (preoperative images), images slices (CT scans), etc. and to reproduce events in multiple views. Image processing module 115 is configured to reconstruct real and virtual images along a real or virtual pathway of a medical device or instrument (or a virtual instrument or device) 102 and/or its surrounding regions. The medical device 102 may include a catheter, a guidewire, a probe, a needle, an endoscope, a robot, an electrode, a filter device, a balloon device, or other medical component, etc. or virtual models or representations of such devices. The device 102 may be employed for initially generating a preoperative image volume 111 of a particular pathway system 148.

An imaging system 110 may be provided for collecting pre-operative imaging data or real-time intra-operative imaging data. The pre-operative imaging may be performed at another facility, location, etc. in advance of any procedure. These images 111 may be stored in memory 116, and may include pre-operative 3D image volumes 111 of a patient or pathway system 148 (real or virtual).

In a particularly useful embodiment, device/virtual device 102 is employed to discover or observe a target. The target may include a lesion, tumor, injury site, object or other target. In another embodiment, the device 102 is not needed at all. Instead, a virtual device or cursor may be employed to chart a course through pathways using virtual or preoperative images (111).

Image processing module 115 includes a pathway determination module or tool 144. The pathway determination module 144 provides user functions for planning navigation along pathways in pre-operative images 111 to plan for interventional procedures. Workstation 112 may include a display 118 for viewing internal images of a subject. The images may include preoperative images, real-time camera images and/or real-time intra-operative images. If an imaging system 110 is employed, the imaging system 110 may include, e.g., a magnetic resonance imaging (MRI) system, a fluoroscopy system, a computed tomography (CT) system, ultrasound (US), etc. Display 118 may also permit a user to interact with the workstation 112 and its components and functions. The display 118 is preferably configured to display one or more panes or view ports 124 in a graphical user interface (GUI) 106. The view ports 124 are preferably correlated such that they are updated simultaneously based on real or virtual trigger events. User interaction with the display 118 is further facilitated by an interface 120. Interface 120 may include hardware devices, such as, a keyboard, mouse, a joystick or any other peripheral or control, may include software devices, such as virtual controls, panels, display panes, etc. or a combination of both devices to permit user interaction with the workstation 112 for pointing control 108.

In one illustrative embodiment, the pathway determination module 144 generates and controls the software devices for interface 120. A mouse or pointer device (108) of the interface 120 may be employed to assist in planning an appropriate path through the pathway system 148, such as airways through a lung. A user may click on the mouse 108 over a specific location to identify the location as a point position on a path to be traversed later in an interventional procedure. The point position may be identified in a two-dimensional slice image, e.g., from a CT scan or the like. Planning may begin at a target site as a first mouse point position. A mouse point position will be defined as a position in a virtual image indicated by a point-and-click type operation using a mouse or similar device. For each new mouse point position in a currently displayed reformat slice, the following steps may be performed using the path planning module 144 to plan a path to be traversed during a subsequently performed procedure.

Figure 2:
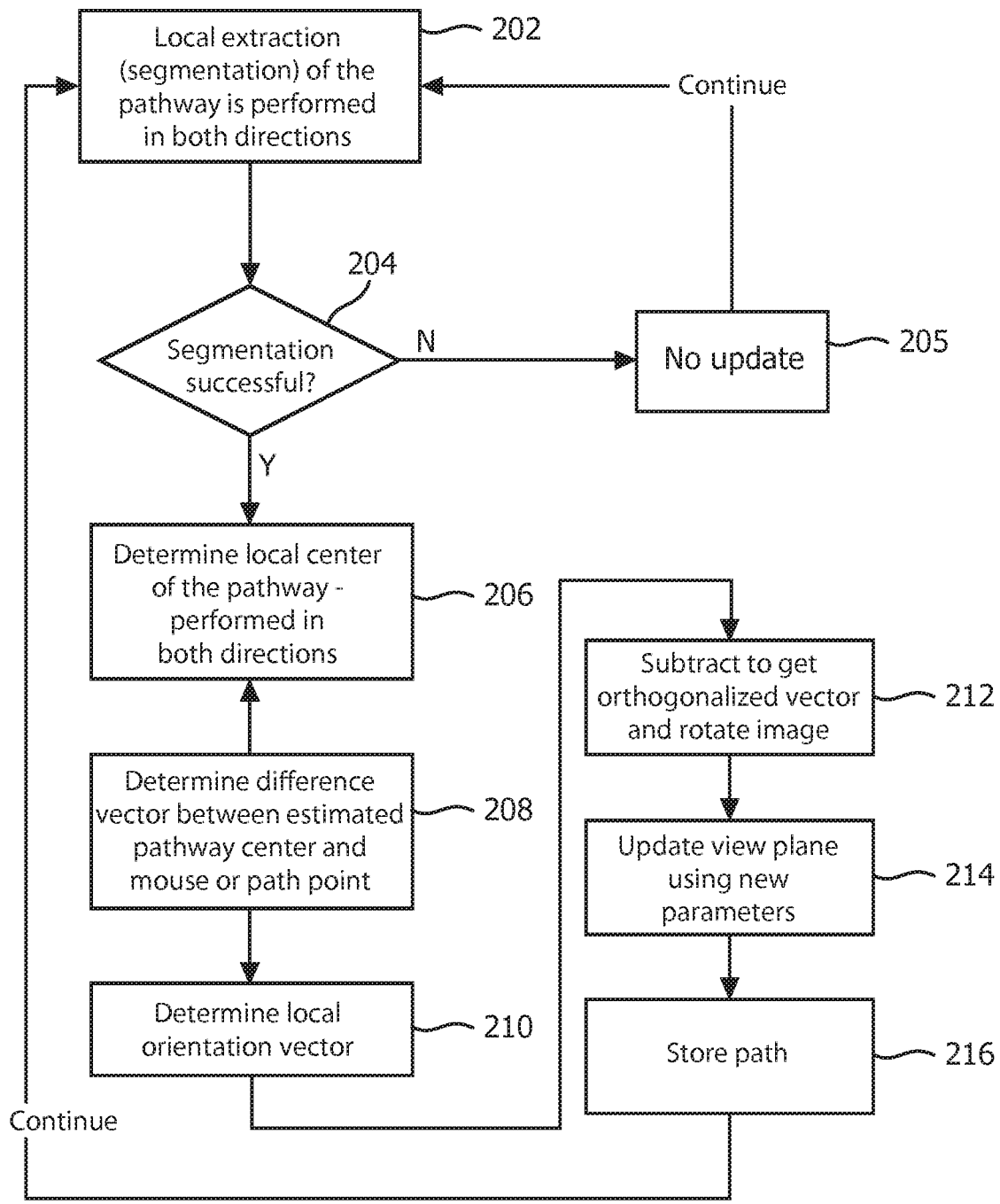
FIG. 2 is a flow diagram showing a method for updating image slices in accordance with a depth of a mouse drawn plan trace in accordance with an illustrative embodiment.

Referring to FIG. 2, a block/flow diagram describes illustrative steps for planning a path through a pathway system. The following steps may be controlled by or carried out by the planning module 144. In block 202, a local extraction (segmentation) of the pathway is performed in both directions (e.g., upstream and downstream). The extraction is preferably performed in pieces of restricted length to ensure real-time computability, using known segmentation algorithms, e.g., a centricity-based region growing algorithm or a tree segmentation and reconstruction algorithm.

In block 204, if the local pathway segmentation is unsuccessful or shows low confidence that the current mouse position is inside the pathway at all, then no update of the current view plane is performed in block 205. Otherwise, in block 206, a local center $c_a$ of the pathway is determined. In block 208, a difference vector $d=c_a-p$ is determined between an estimated pathway center $c_a$ and the current mouse point p, and a projection s is performed where $s=d\cdot n$ projected onto a normal vector n of the currently displayed view plane. Then, the center of the view plane is updated from $c_o$ to $c_o+sn$. In block 210, a local orientation vector $v_a$ of the pathway is determined. In block 212, the vector components of $v_a$ which are parallel to the normal n and a vertical vector $e_v$ of the currently displayed view plane are subtracted to get an orthogonalized vector v. Then, a horizontal vector $e_h$ of the currently displayed view plane is adjusted such that it is aligned with v. To achieve this, the view plane is rotated around a cranio-caudal axis going through the current mouse point p.

In block 214, the currently displayed view plane is updated using the new plane parameters (e.g., vectors). In block 216, all 3D-positions along the path created by mouse drag are traced and stored to use as input for a semi-automated path planning. The path points can be subject to further processing algorithms such as centering and smoothing throughout the process.

Figure 3:
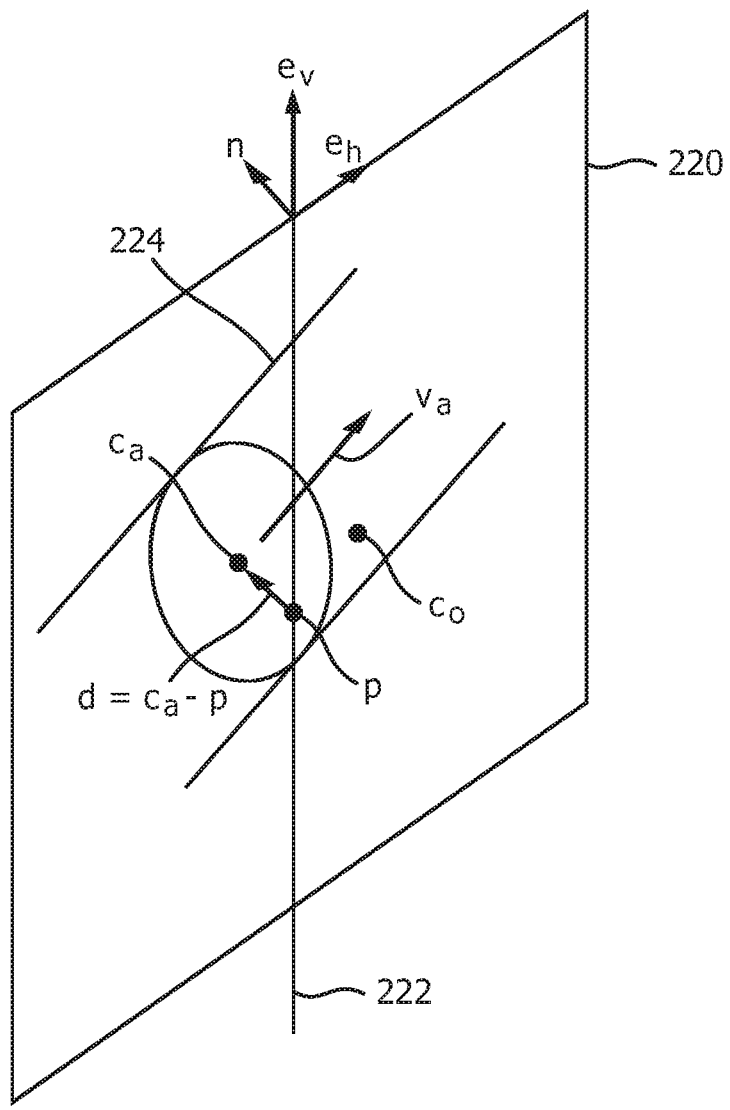
FIG. 3 is a diagram showing vectors for updating a current view plane in accordance with a cursor position (or mouse point) in accordance with one illustrative embodiment.

Referring to FIG. 3, a vector diagram illustratively shows the vector operations described above in accordance with the example work flow of FIG. 2. A current view plane 220 shows a cross-section of a locally segmented airway 224. A local center $c_a$ of the pathway is determined or estimated. A difference vector $d=c_a-p$ is determined between an estimated pathway center $c_a$ and a current mouse point p. A projection s is performed where $s=d \cdot n$ projected onto a normal vector n of the currently displayed view plane 220. Then, a center of the view plane is updated (e.g., from $c_o$ to $c_o+sn$) for better visualization. A local orientation vector $v_a$ of the pathway is determined. The vector components of $v_a$ which are parallel to the normal n and a vertical vector $e_v$ (which is along the cranio-caudal axis 222) of the currently displayed view plane 220 are subtracted to get an orthogonalized vector v (not shown). Then, a horizontal vector $e_h$ of the currently displayed view plane 220 is adjusted such that it is aligned with v. To achieve this, the view plane is rotated around the cranio-caudal axis 222 going through the current mouse point p.

The currently displayed view plane 220 is updated using the new plane parameters (e.g., vectors). After the update, the center point $c_a$ is on the view plane, and the plane normal n is orthogonal to the direction $v_a$. All 3D-positions along the path created by a mouse drag are traced and stored to use as input for a semi-automated path planning. The path points can be subject to further processing (e.g., centering and smoothing). In other words, the path is locally segmented starting from a current mouse position p on the current view (reformat) plane 220, and in a continuous update cycle the reformat plane 220 is shifted back and forth along its plane normal n such that the estimated path center $c_a$ comes to lie in the reformat plane 220, and that the plane 220 is rotated around the cranio-caudal axis 222 such that the normal n of the reformat plane 220 becomes orthogonal to the estimated local path direction.

Referring again to FIG. 1, the path planning module 144 may assist in computing paths using the mouse drag data provided by the user. Pre-operative images 111, such as diagnostic volumetric CT images acquired before the procedure, serve as a "road map" for the procedure and provide very detailed information of the patient's anatomy. These images 111 are employed for planning, e.g., to define the optimal path along airways of a lung, for example, to reach the desired target. In one embodiment, the images 111 are also employed to provide the slices used to update the display 118 when planning a path. The slices are two-dimensional cross-sections that are updated as the mouse is dragged along a path. As the depth changes along the path the slice is updated with a more current slice so that the planning can continue. The slice may be updated based upon the centering information for the mouse point or may be updated manually by the user.

Figure 4A:
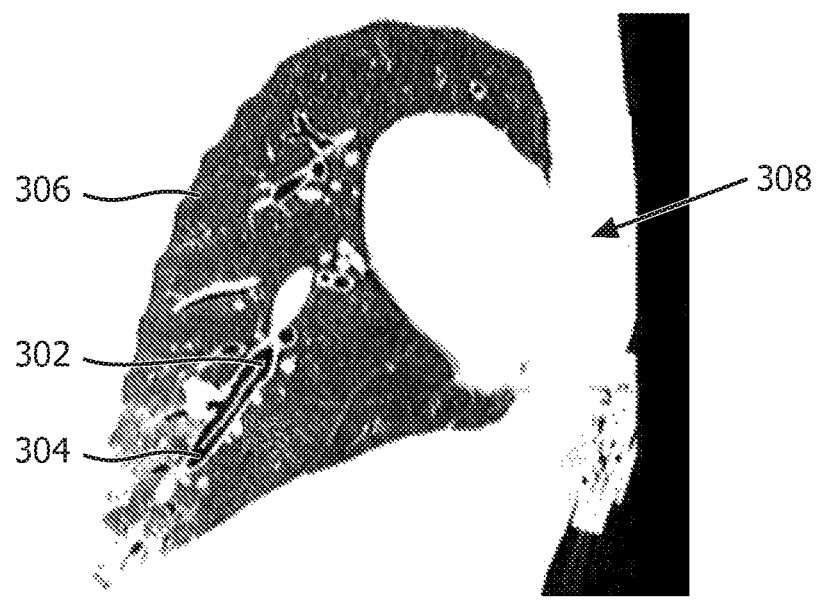
FIG. 4A is an image showing a first slice having a path trace drawn in an endoluminal structure in accordance with another embodiment.
Figure 4B:
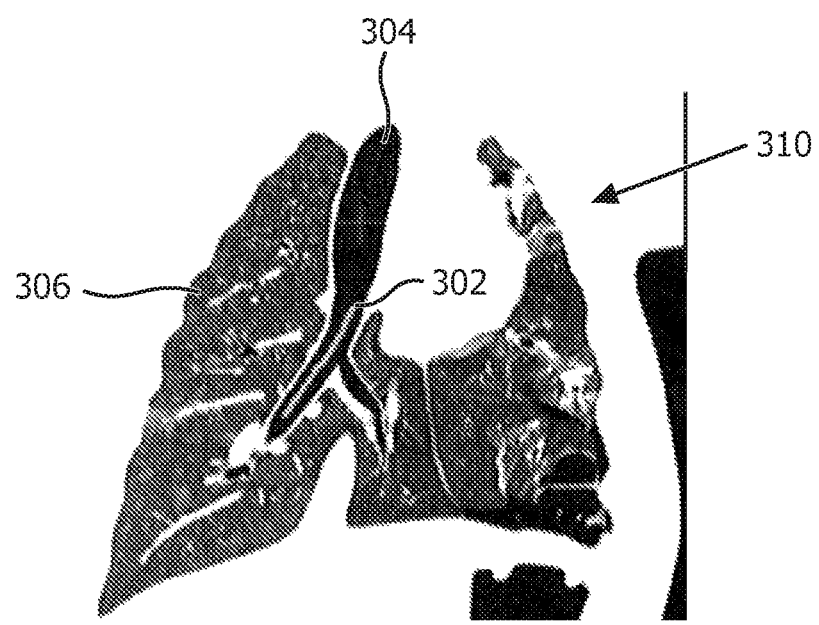
FIG. 4B is an image showing a subsequent slice of a different depth having the path trace extended along the endoluminal structure in accordance with the embodiment of FIG. 4A.

Referring to FIGS. 4A and 4B, two consecutive slices 308 and 310 are illustratively depicted for a lung 306. In accordance with the present principles, the lung 306 is imaged using CT. In FIG. 4A, a mouse point is selected within an airway 304 and dragged along a path to provide a mouse-drag 302. As the mouse drag 302 is extended, it begins to exit the endoluminal portion of the airway 304 in slice 308. The planning path module (144) re-centers the mouse drag 302 and switches a current view to slice 310 in FIG. 4B where the mouse drag 302 can be continued to its destination point. Slice 310 is a next CT scan slice that corresponds with the two dimensional image of slice 308 except that slice 310 has a different depth than slice 308. This permits the mouse drag 302 to be extended further along a desired path by providing additional positions of the endoluminal cavity of airway 304 to be accessible. In addition, the navigation process need only be in two dimensions (in a slice) since the depth (the third dimension) is updated by image processing. This greatly simplifies the planning procedure. It may be preferable to begin the mouse-drag 302 at a target location and work backwards toward an initial start point such as an entry point or port, e.g., the trachea in the case of a lung, etc.

Figure 5:
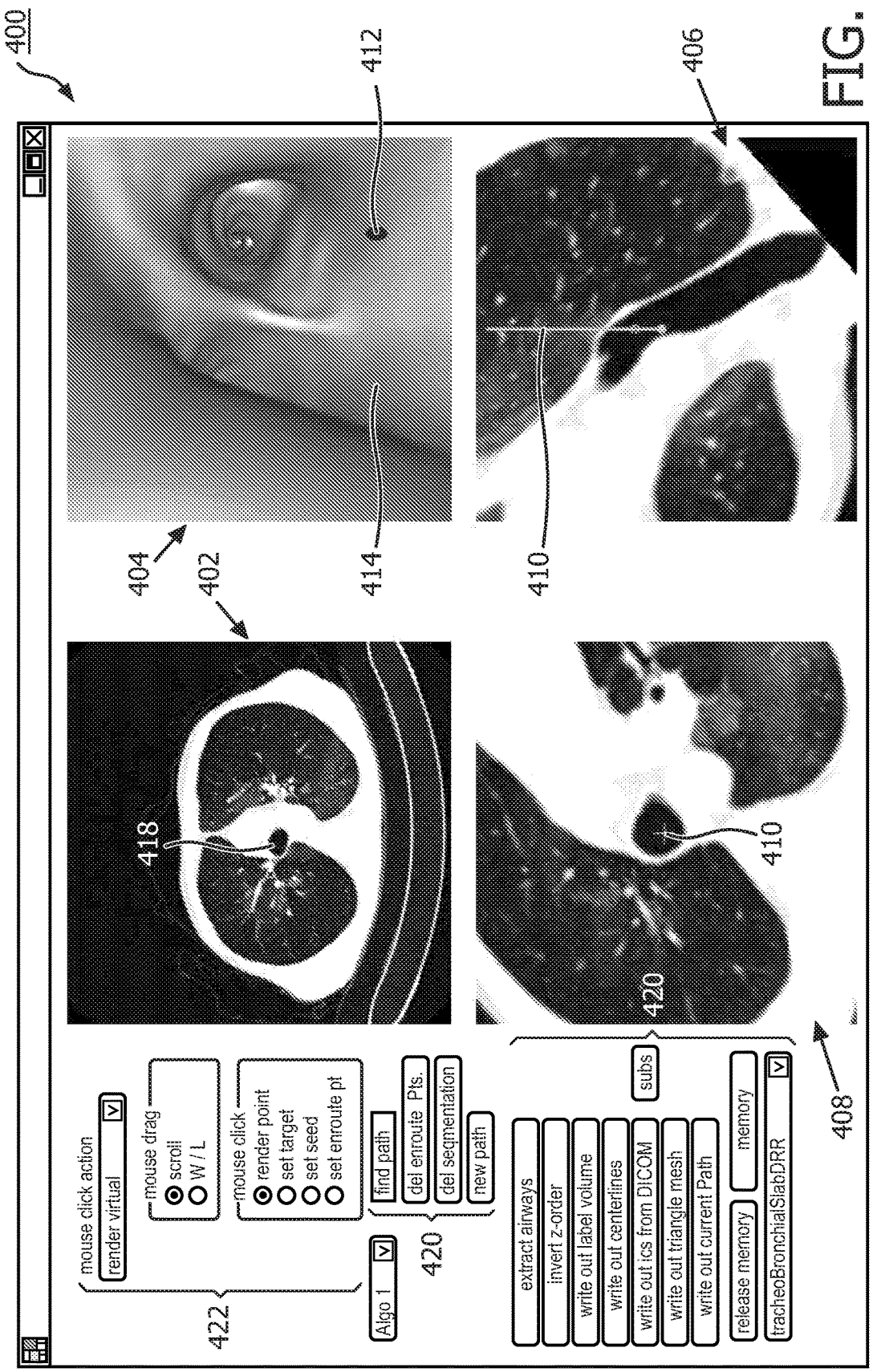
FIG. 5 is a display screen image showing a plurality of viewpoints or panes interrelated with each other using a virtual line reference position in accordance with the present principles.

Referring to FIG. 5, an illustrative graphical user interface (GUI) 400 includes a plurality of viewports 402, 404, 406 and 408. The GUI 400 may be employed in the workstation 112 (FIG. 1), which may include a Bronchoscopy Cockpit or other systems for planning and guiding bronchoscopic procedures. The viewports 402, 404, 406 and 408 are depicted in an illustrative arrangement and a greater or lesser number of viewports may be employed. The viewports 402, 404, 406 and 408 may be configured with different orientations, different sized panes, etc. In the present example, a Standard-View (SV) (axial) is shown in viewport 402. An Endoluminal-View (EV) is shown in viewport 404. One or more obliquely Reformatted-Views (e.g., RV1, RV2, RV3, etc.) are shown in viewports 406 and 408. Viewport 404 includes a pre-operative image volume or a computer generated image volume. The viewports 402, 404, 406 and 408 are preferably all coupled geometrically, as described herein, governed by the underlying notion of a virtual line or needle shown as a needle vector 410. It should be understood that the GUI 400 may be employed for planning navigation for a procedure, or may be employed as a tool during an interventional procedure.

In an illustrative example, a mouse-movement in the Endoluminal-View 404 updates the other viewports 402, 406, 408 in real-time under the proposition that a current mouse point 412 would be the point in an airway wall 414 through which to advance a biopsy needle. The point 412 is determined by a viewing direction of this point in the virtual endoluminal rendering of viewport 404, and an underlying depth value of this point 412 in the virtual endoluminal rendering. Given this airway wall point coordinate, a virtual needle vector is computed as a vector between the airway wall point 412 and a current camera position of the Endoluminal-View 404. Alternatively, another position may be specified instead of the camera position. For example, a mouth position of a working channel of a bronchoscope (rather than the camera position) may be specified as a starting point of the virtual needle. Virtual positions may also be employed.

One oblique Reformatted-View RV1 406 is computed and displayed which shows a plane given by the current endoluminal camera position (in viewport 404) and the needle vector 410. Another Reformatted-View RV2 (not shown) may be computed for a plane which is given by the current endoluminal camera position (in viewport 404) and parallel to the needle vector 410 but orthogonal to RV1 in viewport 406. A third Reformatted-View RV3 408 is computed for a plane which is given by the current endoluminal camera position (in viewport 404) but normal (perpendicular, orthogonal) to the needle vector 410.

The virtual needle 410 is displayed as a line drawing in the Reformatted-Views RV1 (and/or RV2, if shown). The needle 410 is perpendicular to RV3 408 and thus only marked as a single point or cross-hair in RV3 408. The point where the virtual needle 410 penetrates the airway wall is indicated as a marker 418 in the Standard-View 402, and a center-coordinate of Standard-View 402 is reset to this point to center the view and make the trajectory of the virtual needle 410 visible.

A mouse click into the Endoluminal-View 404 may be employed as a method for moving the camera position along in the direction of the endoluminal cavity in the virtual endoluminal rendering. A length of the camera displacement vector is given by a fraction of the underlying depth value of this point in the virtual endoluminal rendering. (The step length fraction can be fixed, say 50%, or user-adjustable.) This ensures that the next camera position will still be inside the airway, regardless of where the user clicks in the Endoluminal-View 404. All viewports are then updated to the new camera position.

It should be understood that the example described above is illustrative and that many variations may be employed in accordance with the present principles. For example, the Standard-View 402 may be axis-parallel in this example; however, the Standard-View 402 may be in axial, coronal, sagittal orientation or all three orientations may be provided simultaneously. The Endoluminal-View 404 may be computed as a direct volume rendering, as a surface rendering from a mesh or as a thresholded volume image. The Reformatted-Views 406, 408 may include a thin-slice reformat, a slab reformat (e.g., maximum intensity or mean intensity), or a direct volume rendering slab. Other variations are also contemplated.

A mouse click in the Standard-View (402) may be employed to trigger a rendering of an Endoluminal-View (404) at the mouse click point. A camera-orientation is automatically estimated for this point using an appropriate local airway extraction algorithm. All viewports are accordingly updated. It should be understood that updating any viewport may trigger the updates of the other views. This update feature may be enabled for all the views or a subset of the views as desired. For example, a mouse click in the Reformatted-View 406 or 408 resets the central point of the Standard-View 402 as well as the camera point of the Endoluminal-View 404 to the selected point, and may update all viewports accordingly. For each airway wall point which is visible in the Endoluminal-View 404, its position may be color-coded in the Reformatted-Views 406, 408 (e.g., RV1, RV2, RV3, etc.) so that the viewing-range of the Endoluminal-View 404 is visible as a boundary contour line in the Reformatted-Views (not shown). In the Endoluminal-View 404, a colored overlay (not shown) may be employed to indicate a maximum angle with which the biopsy needle of a specific bronchoscope can deviate from the camera angle. This feature is useful in aligning the needle for planning a procedure.

In a particularly useful embodiment, mouse wheel movement in the Endoluminal-View 404 may be employed to change a step-length taken when advancing or recessing the camera position by mouse click. A next position following a mouse click with the current step length is indicated as a marker in the Reformatted-Views 406 (and RV2, if employed).

The Reformatted-View RV3 408 may not only be computed through a current camera point but can be computed for any point on the virtual needle 410, so that the user may, e.g., use the mouse wheel to continuously select such a point, thus scrolling through the image volume along (and perpendicular to) the virtual needle 410. A mouse drag (in contrast to mouse click) can be employed in the Endoluminal-View 404 to either turn the camera viewing direction, or change the camera up direction, depending on the direction of the mouse drag.

The GUI 400 includes virtual controls and buttons 420 to provide settings for view selection, orientation, image processing, etc. Controls 422 provide control pointer/mouse options and controls. Other virtual controls, menu boxes, etc. may also be employed.

Figure 6:
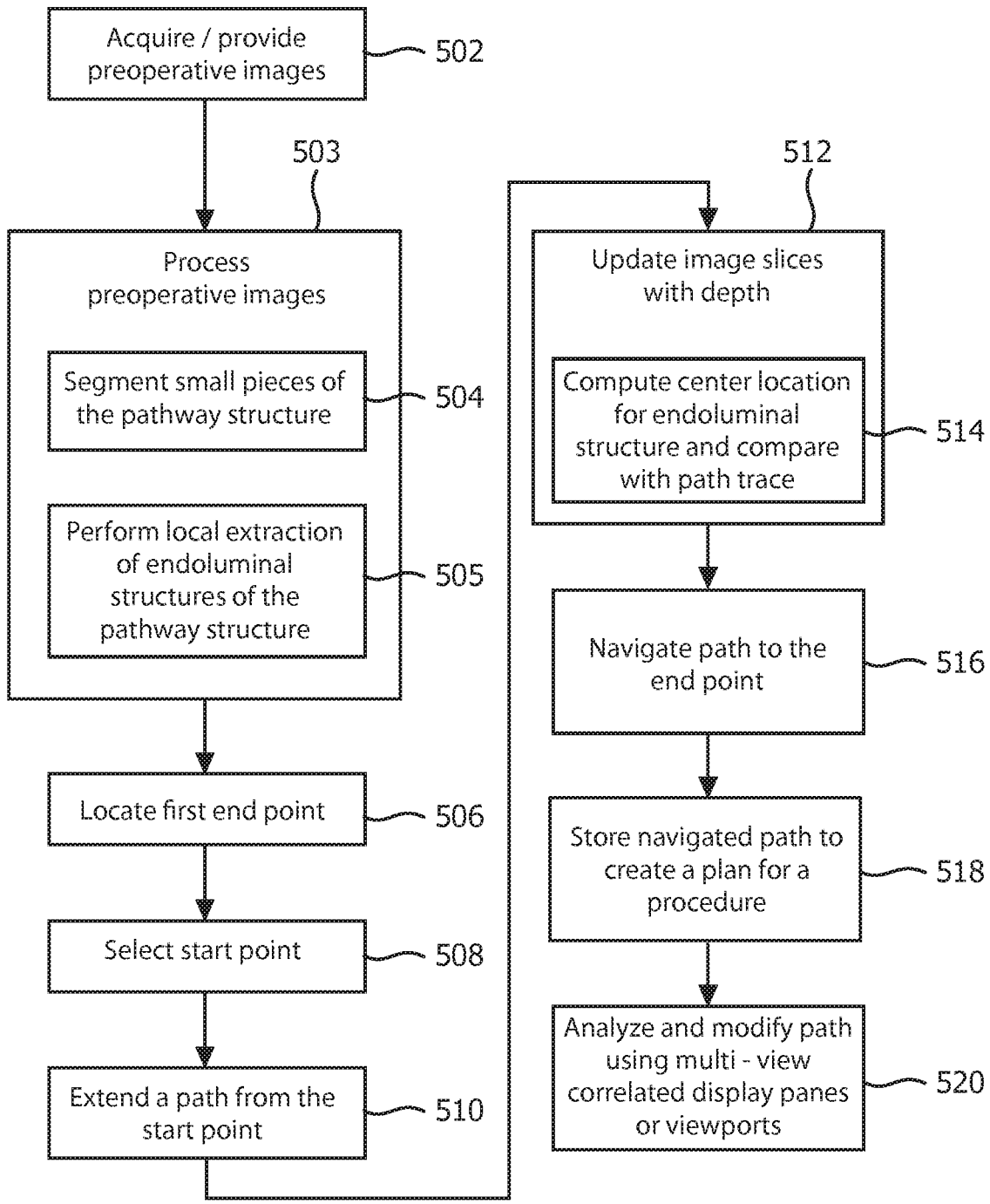
FIG. 6 is a flow diagram showing a method for planning a procedure in accordance with an illustrative embodiment.

Referring to FIG. 6, a block diagram is shown to describe a method for planning a procedure. In block 502, preoperative images are acquired or provided for a pathway structure. This may include a CT scan, magnetic resonance imaging (MRI) scan, etc. anytime in advance of the procedure. In block 503, the preoperative images are processed. In block 504, the pathway structure is segmented in pieces corresponding with a current location of a cursor. The pieces should be small enough to permit real-time computations. In block 505, a local extraction of an endoluminal structure of the pathway structure is preferably performed in two directions about the cursor location.

In block 506, a first end point is located in an image volume of a pathway structure. The image volume is preferably comprised of stacked slices along a depth. The image volume may include a lung, a blood vessel or network, etc. The first end point may include a target to be reached by an interventional procedure, such as a tumor, lesion, injury, etc. In block 508, a start point is selected in the image volume of the pathway structure. The start point selection may include a mouse click to select the start position for a mouse drag. In block 510, a path is extended along the pathway structure. This may include dragging the mouse to extend a visually rendered line in an image of the image volume. While, a mouse click and drag are described other techniques and actions may also be provided.

In block 512, image slices are displayed corresponding with a current position of a depth in the path of the pathway structure. The image slices are updated along the path in accordance with changes in the depth along the pathway structure corresponding with the image slices. In one example, the path is selected along an endoluminal structure. The mouse drag follows a computed centerline of the endoluminal structure. In block 514, a center location is computed for the endoluminal structure in the path, and the center location is compared to a trace of the path to determine whether the stacked slice being viewed should be updated. As the mouse drag continues, the depth of the mouse drag changes to follow the endoluminal structure. As the depth changes, the image slice is updated.

In block 516, the path (via, e.g., mouse drag) is navigated along the pathway to the end point. In block 518, the path is stored for creating a plan for a procedure. In block 520, the path may be analyzed and modified using a motion correlated multi-view display tool and method (see e.g., FIG. 7).

Figure 7:
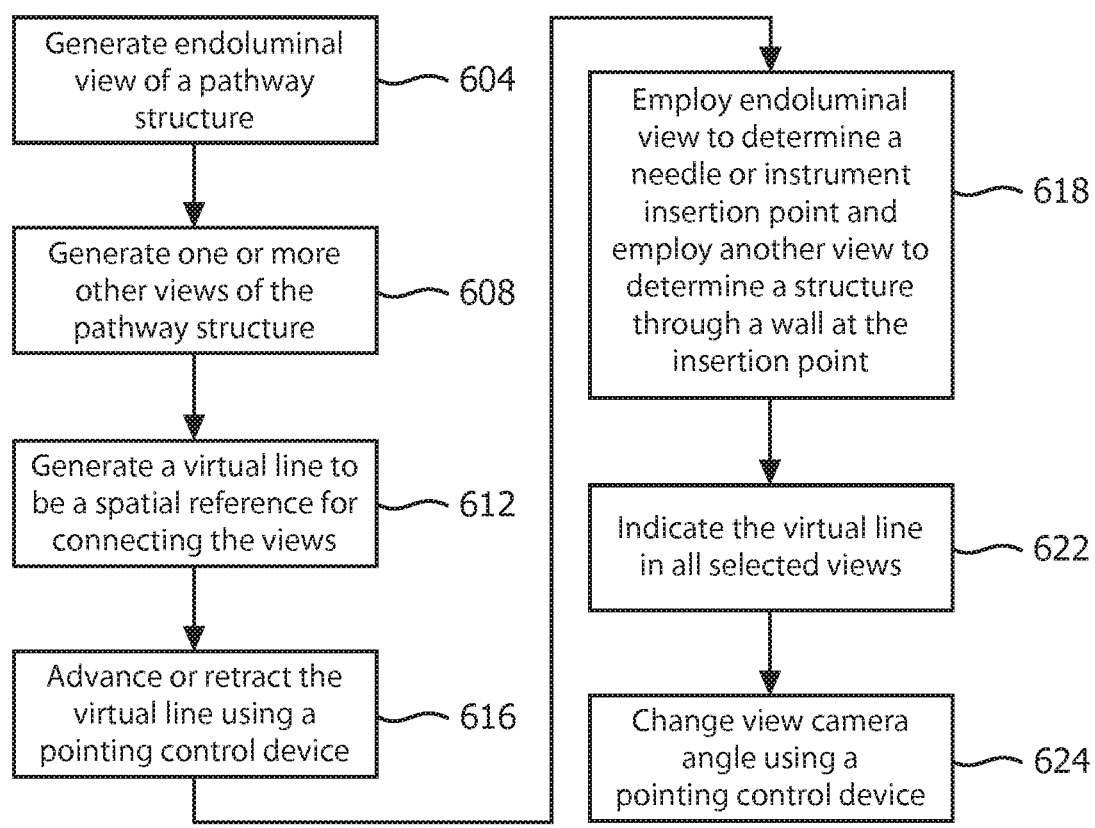
FIG. 7 is a flow diagram showing a method for operatively coupling viewports in accordance with an illustrative embodiment.

Referring to FIG. 7, a method for operatively coupling viewports is shown. The viewports may be employed in a planning procedure; however other applications may also be employed. In block 604, an endoluminal view of a pathway structure is generated in a graphical user interface configured to permit a user to select a path through a pathway system. The endoluminal view may include preoperative images, a computer generated image, an image mesh, etc. In block 608, one or more other views of an image volume are generated. The one or more views may include one or more of a standard view and a reformatted view. The reformatted view may include one of a view parallel to the virtual line or a view perpendicular to the virtual line. The endoluminal and other views are preferably concurrently displayed in a plurality of panes on a display device.

In block 612, the virtual line is generated to provide a spatial reference in a plurality of views including the endoluminal view and the one or more other views. The virtual line is configured to guide the endoluminal view and is employed to provide a reference to concurrently permit updates in all of the views corresponding to a user selected position update of the virtual line. Image information surrounding the virtual line in the views is concurrently viewable in the user interface. In block 616, the virtual line is advanced or retracted in the endoluminal view or other view by advancing or withdrawing a pointing control device. All selected views are accordingly updated. In block 620, in one embodiment, the endoluminal view is employed to determine a needle insertion point in a wall of the endoluminal structure and at least one other view is employed to determine a structure through the wall not visible in the endoluminal view. The virtual line may be employed to model a biopsy needle or other instrument. Other views and uses of the correlated viewports may be provided in accordance with the present principles. In block 622, the virtual line is preferably indicated in all selected views.

In block 624, a camera angle for at least one of the views may be changed using a pointing control device. The pointing control device may include a mouse or equivalent device. The camera control may be provided by a mouse wheel or the like.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for automatic depth scrolling and orientation adjustment for semi-automated path planning (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A planning system, comprising:
a processor;
memory coupled to the processor and storing a planning module; and
a user interface coupled to the processor and configured to permit a user to select a path through a pathway system by controlling a displayed cursor point;
the planning module configured to upload two or more slices of an image volume corresponding to the displayed cursor point and provide an automatic adaptation of depth, position and orientation, such that as the path is navigated by controlling the displayed cursor point, the two or more slices are updated continuously to automatically change a view plane and orientation of the slices based on changes in a position of the displayed cursor point in response to a user interaction changing the position of the displayed cursor by moving a mouse or pointing device of the graphical user interface.

2. The system as recited in claim 1, wherein the planning module is configured to generate a trace line to indicate the path.

3. The system as recited in claim 1, wherein the pathway system includes a lung and the path is determined between an entry point and a target within the lung.

4. The system as recited in claim 1, wherein the displayed cursor point is centered within a depth dimension of an endoluminal structure and the planning module checks the depth with images slices to determine whether the image slice should be updated.

5. The system as recited in claim 1, further comprising an image processing module configured to perform a local extraction of an endoluminal structure of the pathway in two directions about a cursor location.

6. The system as recited in claim 1, wherein the memory stores all three-dimensional positions along the path created by a drag of the cursor point to employ as input for path planning.

7. The system as recited in claim 1, wherein the image volume includes pre-operatively collected images.

8. A system having operatively coupled viewports, comprising:
a processor;
memory coupled to the processor and storing an image processing module;
a graphical user interface coupled to the processor and configured to permit a user to select a path through a pathway system;
the image processing module being configured to render:
an endoluminal view of the pathway, and
one or more other views of an image volume; and
a virtual line to provide a spatial reference in all of the views including the endoluminal view and the one or more other views;
a user-controlled cursor point configured to guide the endoluminal view wherein when the cursor point is moved in any of the views in response to a user interaction with the system via the graphical user interface all of the other views are automatically updated to change a view plane and orientation in the other views such that image information surrounding the user-controlled cursor point in the other views is concurrently viewable in the user interface.

9. The system as recited in claim 8, wherein the one or more views includes one or more of a standard view and a reformatted view.

10. The system as recited in claim 8, wherein a reformatted view includes one of a view parallel to the virtual line or a view perpendicular to the virtual line.

11. The system as recited in claim 8, wherein the virtual line is advanced or retracted in the endoluminal view by advancing or withdrawing a pointing control device.

12. The system as recited in claim 8, wherein the endoluminal view is employed to determine a needle insertion point in a wall of the endoluminal structure and at least one other view is employed to determine a structure through the wall not visible in the endoluminal view.

13. The system as recited in claim 8, wherein the virtual line is indicated in all the selected views.

14. The system as recited in claim 8, further comprising a pointing control device configured to change a camera angle for at least one of the views.

15. The system as recited in claim 8, wherein the graphical user interface includes a display such that a plurality of panes corresponding to multiple views is concurrently displayed.

16. A method for planning a procedure, comprising:
locating an end point in an image volume of a pathway structure, the image volume comprised of stacked slices along a depth;
selecting a start point in the image volume of the pathway structure by controlling a displayed cursor point;
extending a path along the pathway structure;
updating image slices of the pathway structure along the path continuously to automatically change a view plane and orientation based on a position of the displayed cursor point in accordance with a depth of the pathway structure corresponding with the slices;
navigating along the pathway to the end point and providing an automatic adaptation of depth, position and orientation; and
storing the path for creating a plan for a procedure.

17. The method as recited in claim 16, further comprising segmenting the pathway structure in pieces corresponding with a current location of a cursor.

18. The method as recited in claim 16, wherein the pathway structure includes an airway of a lung and the path is determined between a target as the start point and a trachea as the end point.

19. The method as recited in claim 16, further comprising computing a center location for an endoluminal structure in the path and comparing the center location to a trace of the path to determine whether the stacked slice being viewed should be updated.

20. The method as recited in claim 16, further comprising performing a local extraction of an endoluminal structure of the pathway structure in two directions about a cursor location.

21. The method as recited in claim 16, wherein the image volume includes pre-operatively collected images.

22. A method for operatively coupling viewports, comprising:
generating an endoluminal view of a pathway structure in a graphical user interface configured to permit a user to select a path through a pathway system by controlling a displayed cursor point and providing an automatic adaptation of depth, position and orientation;
generating one or more other views of an image volume continuously;
using only a change of position of the displayed cursor point in any one of the views, in response to a user interaction changing the position of the displayed cursor in the any one view by moving a mouse or pointing device of the graphical user interface, to automatically change a view plane and orientation of all of the other views; and;
generating a virtual line to provide a spatial reference in a plurality of views including the endoluminal view and the one or more other views such that the virtual line is configured to guide the endoluminal view and is employed to provide a reference to permit updates in the other views corresponding to a user selected position update of the virtual line such that image information surrounding the virtual line in the other views is concurrently viewable in the user interface.

23. The method as recited in claim 22, wherein the one or more views includes one or more of a standard view and a reformatted view.

24. The method as recited in claim 22, wherein a reformatted view includes one of a view parallel to the virtual line or a view perpendicular to the virtual line.

25. The method as recited in claim 22, wherein the virtual line is advanced or retracted in the endoluminal view by advancing or withdrawing a pointing control device.

26. The method as recited in claim 22, wherein the endoluminal view is employed to determine a needle insertion point in a wall of the endoluminal structure and at least one other view is employed to determine a structure through the wall not visible in the endoluminal view.

27. The method as recited in claim 22, wherein the virtual line is indicated in all selected views.

28. The method as recited in claim 22, further comprising changing a camera angle for at least one of the views using a pointing control device.

29. The method as recited in claim 22, wherein the endoluminal and other views are concurrently displayed in a plurality of panes.

* * * * *